United States Patent [19]

Kriese et al.

[11] 3,957,374
[45] May 18, 1976

[54] APPARATUS FOR OBTAINING SAMPLES OF DUSTS FOR ANALYSIS BY SPECTROCHEMICAL EXAMINATION

[75] Inventors: Manfred Kriese, Heidenheim; Jurgen Kuhl, Aalen; Siegfried Neumann, Unterkochen; Reimund Torge, Aalen, all of Germany

[73] Assignee: Carl Zeiss-Stiftung, Oberkochen, Germany

[22] Filed: Jan. 14, 1975

[21] Appl. No.: 541,049

[30] Foreign Application Priority Data
Feb. 1, 1974  Germany............................ 2404873
July 22, 1974  Germany............................ 2435091

[52] U.S. Cl.................................. 356/85; 55/154; 356/36; 356/244
[51] Int. Cl.² ...................... G01N 1/00; G01J 3/42
[58] Field of Search..................... 55/141, 152, 154; 356/38, 36, 85-87, 244, 246

[56] References Cited
UNITED STATES PATENTS

| | | |
|---|---|---|
| 2,868,318 | 1/1959 | Perkins et al. .................... 55/154 X |
| 3,419,359 | 12/1968 | Anderson et al. ............... 356/87 UX |
| 3,431,411 | 3/1969 | Harrick ................................ 356/38 |
| 3,702,219 | 11/1972 | Braun et al. ...................... 356/85 X |
| 3,768,258 | 10/1973 | Smith et al. ...................... 55/152 X |
| 3,832,060 | 8/1974 | Dahlquist.......................... 356/85 X |
| 3,873,205 | 3/1975 | Thompson .......................... 356/85 |
| 3,879,986 | 4/1975 | Sehmel .............................. 55/154 X |

Primary Examiner—John K. Corbin
Assistant Examiner—F. L. Evans
Attorney, Agent, or Firm—Nichol M. Sandoe

[57] ABSTRACT

Samples of fine dusts in air or gases are collected for analysis and measurement by atomic absorption or atomic fluorescence by conducting the air or gases across a surface of a sample container and causing the dust to be deposited electrostatically on the said surface. The sample container is then heated to a temperature sufficient to vaporize the particles of dust, and the vaporized particles are then brought into the beam path of an atomic absorption or atomic fluorescence spectrometer.

3 Claims, 12 Drawing Figures

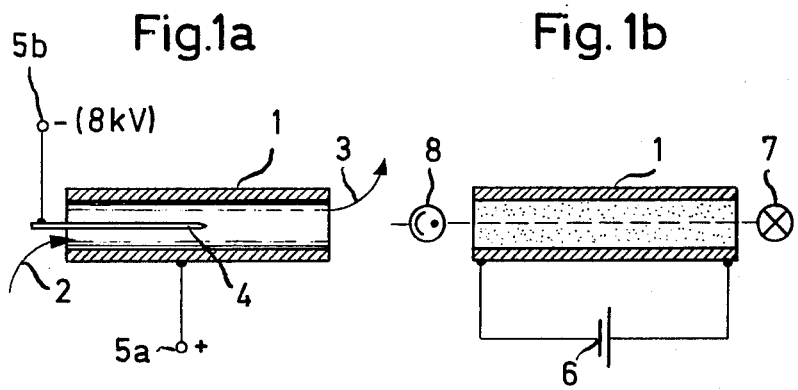
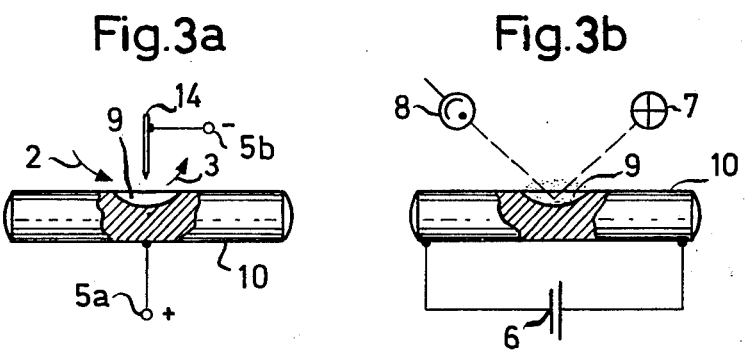
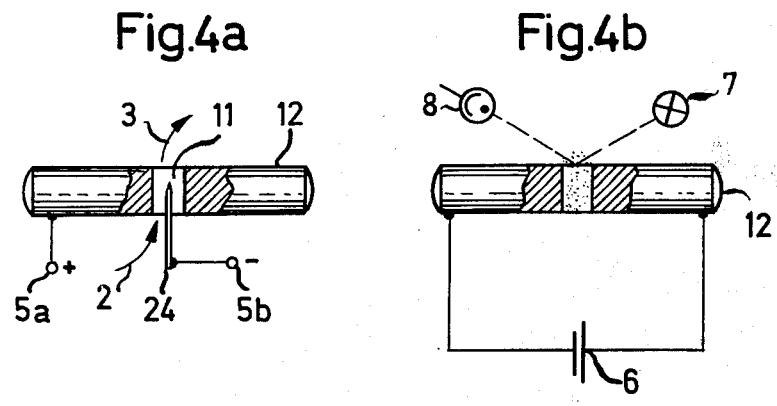

APPARATUS FOR OBTAINING SAMPLES OF DUSTS FOR ANALYSIS BY SPECTROCHEMICAL EXAMINATION

This invention relates to a method and apparatus for the analysis and measurement of fine dusts in air and gases and in particular to a method and apparatus for obtaining samples of such fine dusts for analysis and measurement thereof by means of atomic absorption or atomic fluorescence.

In the analysis of fine dusts in gases, the ability to produce representative samples is of basic importance.

It is known to use atomic absorption and atomic fluorescence analysis for the determination of very small quantities of chemical elements. It is furthermore known to place samples dissolved in a solvent in a graphite cell and then to heat the graphite cell by electric resistance heating until the solvent is evaporated. Thereupon the sample to be measured is vaporized by heating the graphite cell in a few seconds to a temperature of up to 2600°C. In the beam path of a spectrometer signals are obtained from the vaporized sample by atomic absorption or atomic fluorescence, these signals being characteristic of the elements contained in the sample (Spectrochemica Acta 1968, Vol. 23$b$, pages 215–226).

It is also known in the prior art to use filters for collecting samples from a volume of gas or from the air. Examples of such filters are the MF-Millipore filters which consist of pure cellulose esters. The collected deposit of dust is thereupon digested chemically and the digested sample thus obtained is analyzed by known methods of non-flame atomic absorption (Anal. Chim. Acta 55, 439 (1971) P. Hermann, Collogn. Spectroscopicum Internationale XVII, Florence, 1973, Acta Vol. 11, 693).

In an improved method (Analytical Chemistry, Vol. 45, No. 9, August 1973, pages 1606–1609) a filter is placed in a graphite cell and the air or gas to be examined is pumped through the filter. As a result of the very high detection sensitivity of the graphite vaporizer, small amounts of air are sufficient for the analysis and only short pumping times are required for collecting the sample. This method, however, has the disadvantage that the filter must be incinerated prior to the analysis of the solids contained in the air. Furthermore, the filter may contain traces of the element to be analyzed so that for each measurement a false value which is dependent on the filter must be taken into account.

The object of the present invention is to provide a method for the obtaining of samples, and an apparatus suitable for carrying out the method, as a result of which time consuming intermediate steps which are the cause for errors in measurement, such as the incinerating of the filter and determination of a false value, are eliminated. This object is achieved in accordance with the invention by conducting the gas which is to be examined directly across the surface of an electrically heatable sample container, by causing the fine dust contained in the gas to be deposited electrostatically on the surface of the sample container, by heating the sample container to a temperature sufficient to vaporize the particles of dust, and by bringing the said vaporized particles into the beam path of an atomic absorption or atomic fluorescence spectrometer.

In one suitable apparatus for carrying out the method of the invention, the sample container comprises a graphite tube into which an ion generator comprising a needle shaped electrode for corona discharge is introduced.

Instead of a single electrode, a bundle of needle shaped electrodes can also serve as an ion generator.

Such electrodes are advantageously made of metal wire and may be provided with electrolytically etched tips.

It is furthermore advisable to surround the electrodes with an insulating jacket over a portion of their length.

In another suitable apparatus for carrying out the method of the invention, the sample container comprises a graphite bar above which an electrode for corona discharge is arranged. The gas to be examined is moved over the surface of the graphite bar and the particles of dust contained in the gas are fixed by the corona discharge to the surface of the bar located below the electrode.

For better localizing of the dust particles to be examined, a depression in the surface of the bar may be provided, arranged centrally below the electrode.

A constriction of the graphite bar at the place of the deposit of the sample causes the highest temperature of the bar to occur at this very point.

In another suitable embodiment of apparatus for carrying out the method of the invention, the sample container comprises a graphite bar having a cylindrical bore therein into which the corona discharge electrode extends.

In another advantageous embodiment of apparatus for carrying out of the method of the invention, the sample container is separated in space from the ion generator. Separation in space can be produced by a connecting piece. Such a connecting piece may consist, for example, of a tube having two branches. The gas to be examined is introduced through one branch of the connecting piece while an ion generator is located in the other branch. A particular advantage of this separation in space is that the optical path of the beam is not obstructed by the electrode. A series of measurements can thus be carried out by continuous interchange between sampling and atomic absorption analysis one after the other without moving any essential parts mechanically. This embodiment is particularly well suited for use in a relatively simple automated system for carrying out the entire measuring process.

It may furthermore be advantageous to arrange a plurality of sample containers on a magazine belt, a magazine carrier being provided to receive the magazine belt which said carrier has an inlet connection for the introduction of the gas to be examined and an oppositely disposed inlet connection for receiving the ion generator. A motor with automatic control may be provided for advancing the magazine belt and for the simultaneous forward and backward movement of the inlet connections.

The use of a magazine belt with a magazine carrier permits automatic sampling at any desired place, separated locally from the analytical instrument. The apparatus is therefore also particularly well suited for measurements at endangered work places.

A particular advantage obtained from the use of the invention is that the use of a filter is unnecessary and, thus, the measuring of a false value is no longer necessary. Furthermore, the method is characterized by the extremely short time required for collecting a sample, i.e., about one minute per sample. As compared with the prior art, the consistency and precision of measurement within an error of ± 2.5% is also a substantial advantage. The method of the invention also makes it possible, for example, to measure dependably impurities in the air which occur and disappear within 10 minutes. The high efficiency of disposition of impurities and the possibility of using the apparatus for series measurements constitute further advantages.

Examples of suitable apparatus for carrying out the method of the invention are shown in the drawings and are described in further detail hereinafter.

In the drawings:

FIG. 1a shows a sample cell comprising a graphite tube for collecting the sample;

FIG. 1b shows the sample cell of FIG. 1a during the analysis;

FIG. 3a shows a sample container comprising a graphite bar with an electrode arranged above the bar;

FIG. 3b shows the container of FIG. 3a during the analysis;

FIG. 4a shows a sample container comprising a graphite bar, in which the electrode extends into a bore hole in the bar;

FIG. 4b shows the sample container of FIG. 4a during the analysis;

Figure 7:
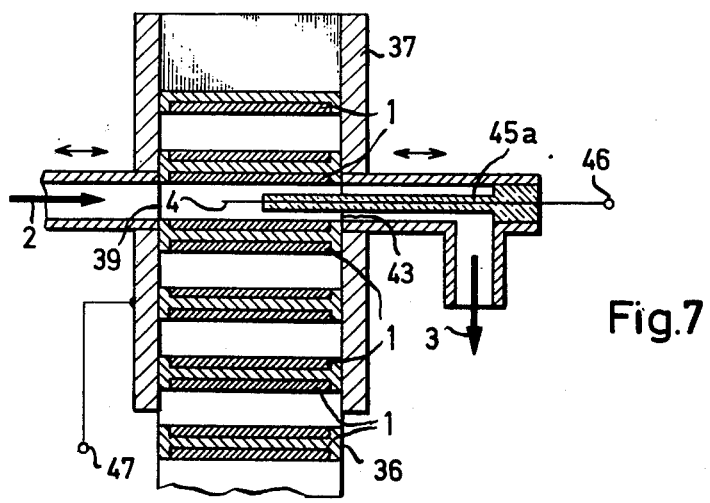
FIG. 7 shows a magazine container adapted to receive a series of sample containers arranged on a magazine belt.

In FIG. 1a, 1 is a graphite tube into which a needle shaped electrode 4 extends which is connected at the terminals 5a and 5b to a source of high voltage electric current available either from batteries or from a power line. The voltage required for the corona discharge from the electrode 4 is not more than about 5 KV; the current flowing through the electrode amounts to about 0.5 mA so that a power of about 2.5 watts is consumed by the high voltage apparatus. The air or gas to be examined is pumped into the graphite tube 1 in the direction indicated by the arrow 2 and leaves the tube 1 in the direction of arrow 3 after the particles contained therein have been negatively charged by the corona discharge of the electrode 4 and have been deposited thereby on and fixed to the positively charged wall of the tube. The circuit 6 serves to heat the graphite tube through which an electric current of not more than 400 amperes flows for this purpose. In this way, the graphite tube will, within a few seconds, reach a temperature of maximum 2600°C, which is sufficient to vaporize the sample which has been electrostatically deposited on the tube. In FIG. 1b, 7 is a source of primary light for atomic absorption and 8 is the receiver of a spectrometer, the beam path of which is positioned to intercept, analyze and measure said vaporized particles.

Figure 2:
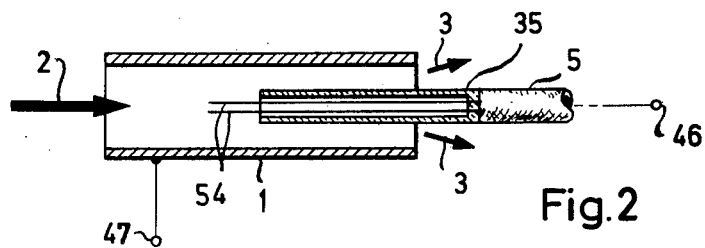
FIG. 2 shows a sample container comprising a graphite tube having an ion generator comprising a plurality of electrodes.

In FIG. 2, 54 is a bundle of several electrodes which may consist, for example, of four to ten individual electrodes which are connected to one pole 46 of a source of high voltage current while the graphite tube 1 is connected to the other pole 47. The pole of the source of high voltage which is connected with the graphite tube vai a resistor is in any event grounded. An insulating jacket 35 surrounds the bundle of electrodes.

In FIG. 3a, 10 is a graphite bar with a high voltage electrode 14 located centrally above it. The air or gas to be examined is conducted in the direction indicated by arrows 2 and 3 over the surface of the bar 10 which is acted upon by the corona discharge of the electrode 14. In order better to localize the electrostatically deposited particles, the surface covered by the electrode 14 is preferably formed as a depression 9 in the bar 10. The particles contained in the air or gas which are deposited on the surface of the depression 9 can be vaporized as previously described and analyzed and measured by the spectrometer arrangement shown in FIG. 3b.

In the apparatus of FIG. 4a, a graphite bar 10 is provided with a cylindrical bore hole 11. A high voltage electrode 24 extends into this cylindrical bore hole. The air or gas to be examined is conducted through the bore hole in the direction indicated by arrows 2, 3. The particles contained in the air or gas are deposited on the wall of the bore hole by the corona discharge of the electrode 24 and can then be vaporized as previously described and analyzed and measured in the spectrometer arrangement shown in FIG. 4b.

Figure 5A:
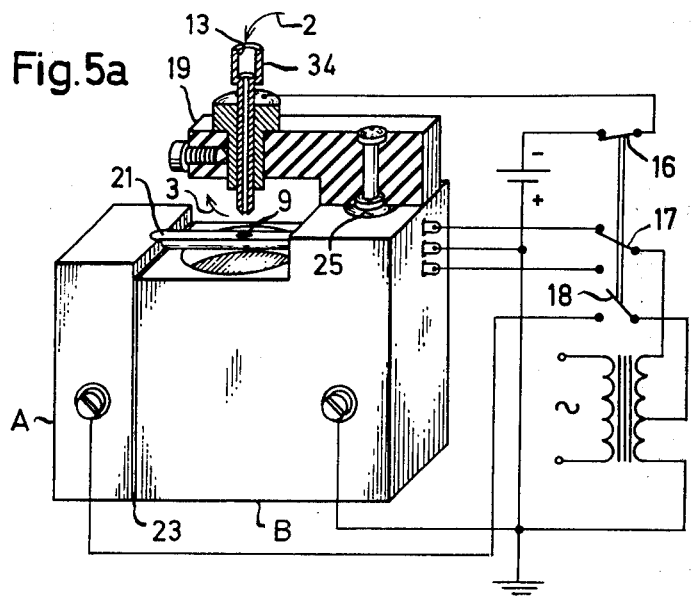
FIG. 5a is a perspective view of an apparatus for carrying out the method, during the collecting of the sample.
Figure 5B:
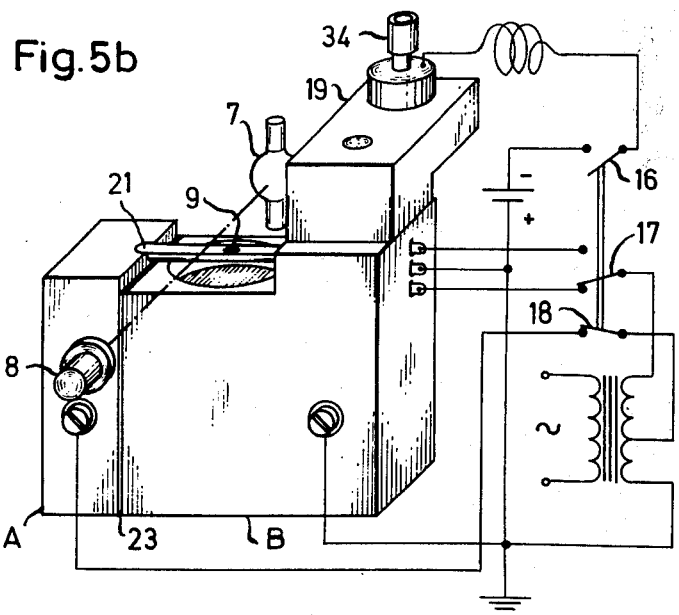
FIG. 5b shows the apparatus of FIG. 5a as arranged during the analysis.

In the perspective view of the apparatus shown in FIGS. 5a and 5b, the electrode 34 comprises a hollow needle having an air inlet opening 13. The electrode 34 is mounted in a pivotally mounted insulating support 19 which extends across and above a graphite bar 21 which is the sample container. The metal blocks A and B are separated by an insulating layer 23 and are connected conductively with each other by the graphite bar 21. A rotary magnet 25 is mounted in the electrode support 19. In the position of the rotary magnet shown in FIG. 5a, the electrode 34 is located above the graphite bar 21, and the switch 16 is closed for applying high voltage to the electrode 34. The switch 18 for controlling the circuit for heating the bar 21, which switch is mechanically connected with the switches 16 and 17, is open. The switch 17 is a pulse switch which provides, upon actuation, in each case, only a short contact. The air to be examined is pumped through the electrode 34 in the direction indicated by arrows 2, 3 by a pump, not shown in the drawing.

In FIG. 5b, the electrode support 19 has been swung away to permit the analysis of the sample collected. This is achieved by opening the switch 16. The pulse switch 17 is closed thereby and provides a brief impulse which causes the rotary magnet 25 to be turned 90° and swings the support 19 into the position shown in FIG. 5b. At the same time, the mechanically connected switch 18 is closed and the heating current heats the graphite bar 21 to the temperature required for the vaporization of the sample.

Figure 6:
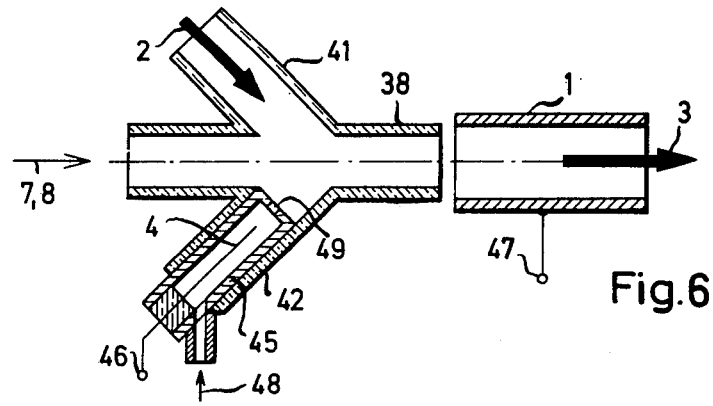
FIG. 6 shows a construction in which the sample container and ion generator are spacially separated by an intermediate piece.

In FIG. 6, the optical beam path of an analyzer consisting primarily of a primary source of light 7 and a spectrometer receiver 8, is designated by a broken line. A connecting piece 38 is provided with two branches 41, 42. An ion generator 45 is mounted in the branch 42 while the branch 41 provides an inlet for the air or gas to be examined. In the embodiment shown in FIG.

6, the longitudinal axis of the connecting piece 38 coincides with the longitudinal axis of the graphite tube 1 and with the optical beam path of the analyzer 7, 8. Compressed air is introduced into the ion generator 45 through the opening 48 and under its action the ions produced are carried along through the opening 49 and impinge upon the sample of gas fed at 41. The solid or liquid particles contained in the sample of gas are thereby charged and deposited on the graphite tube 1.

In FIG. 7, 37 is a magazine carrier and 36 a magazine belt. The magazine carrier is provided with an inlet 39 for the air or gas to be examined and with an opening 43 to receive an ion generator 45a whose electrode extends into the graphite tube 1 which is to be examined. In one suitable embodiment a magazine belt having the dimensions of 20 × 32 × 220 mm could receive twenty tubes. The advance of the magazine belt and the alternating sidewise movements (indicted by arrows) of the gas inlet and corona-discharge-electrode inlets 39, 43 which are coupled therewith can be effected by a motor with suitable automatic control in the same manner as the transport of an ordinary magazine in slide projectors. 46 and 47 are the terminals of a high voltage generator.

Figure 8:
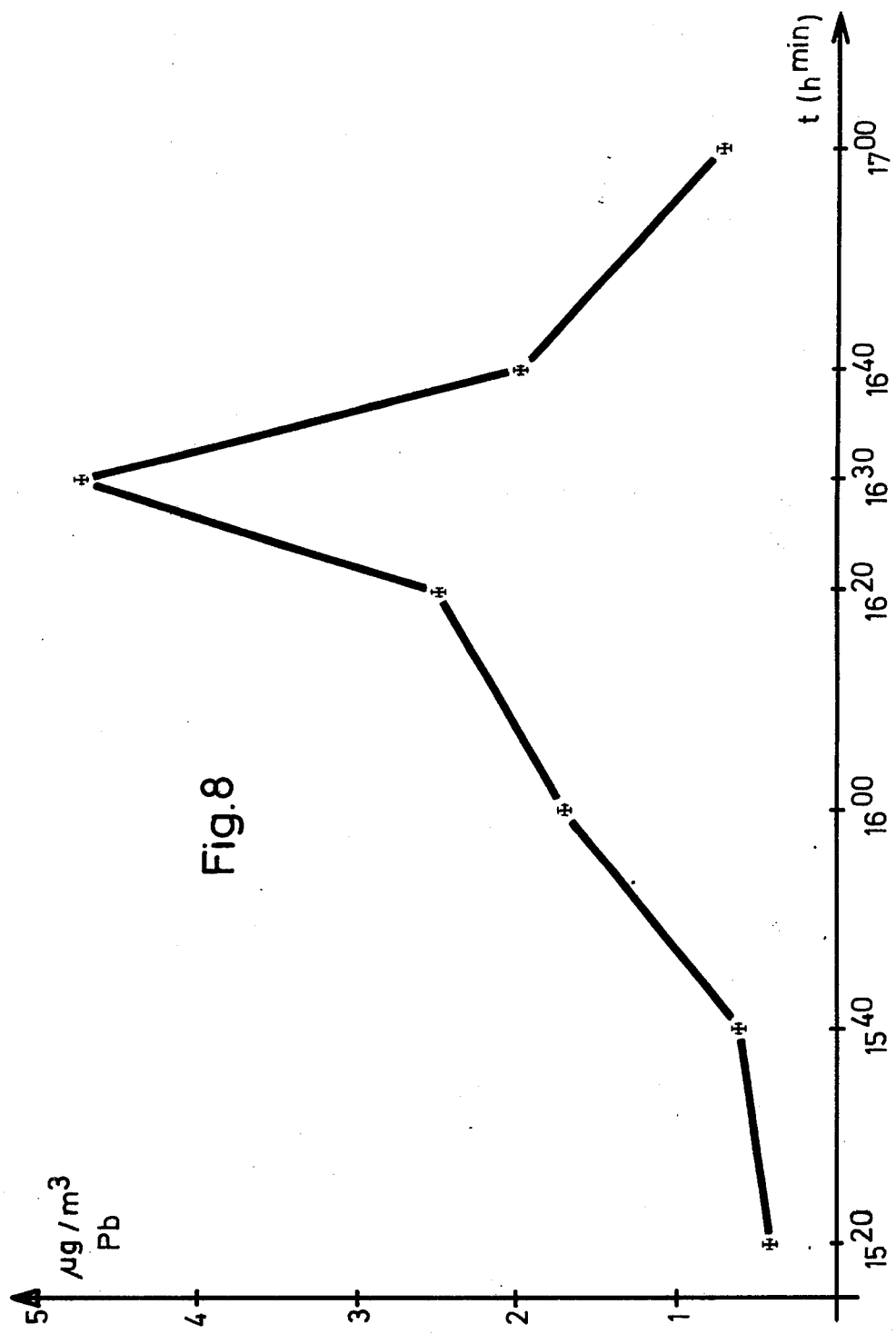
FIG. 8 is a graph which shows the lead content of the air at a place of heavy traffic measured in accordance with the invention, plotted against the time of the day.

An example of measurement of results obtained by use of the method of the invention are plotted in FIG. 8. The lead content of the air which occurs as a function of the closing time of business at the exit of a large industrial parking lot was examined. In the graph, the lead content of the air has been plotted in micrograms per cubic meter on the y-axis and time on the x-axis. With a staggered termination of working hours commencing at 3:20 p.m. and peaking at about 4:30 p.m., the greatest contamination of the air by lead is found at the time of the greatest density of traffic. The advance provided by the method of the invention can be noted from the limits of error indicated in the drawing. With a sample collecting time of only one minute, the precision of measurement is ±2.5%.

What is claimed is:

1. Apparatus for obtaining samples of dusts for analysis by spectrochemical examination comprising a sample container, an ion generator for electrostatically charging dust particles contained in air adjacent the surface of said sample container, means for electrostatically charging the sample container positively, means for electrostatically charging the ion generator negatively, means including a circuit for heating said sample container electrically, and a double-throw switch for connecting said sample container either to a source of high voltage electric current for electrostatically depositing the dust particles on said sample container or alternatively to said heating circuit for atomizing the deposited dust particles, said ion generator being mounted on a swivel device which allows the ion generator to swing away to expose said sample container to a light source for spectrochemical examination of said atomized dust particles.

2. Apparatus as claimed in claim 1 in which said sample container comprises a graphite bar and in which said ion generator comprises a corona discharge electrode located above said bar.

3. Apparatus as claimed in claim 1 in which said swivel device is actuated by electromagnetic means including a circuit which is energized when said heating curcuit is energized.

* * * * *